United States Patent
Fitzgerald et al.

(10) Patent No.: US 9,718,843 B2
(45) Date of Patent: Aug. 1, 2017

(54) LOW PH SYSNTHESIS OF ZINC-LYSINE COMPLEX

(71) Applicant: Colgate-Palmolive Company, New York, NY (US)

(72) Inventors: Michael Fitzgerald, New Brunswick, NJ (US); Joseph Convery, Jackson, NJ (US); Harsh Trivedi, Hillsborough, NJ (US); Lisa Manus, New Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/319,423

(22) PCT Filed: Jun. 18, 2014

(86) PCT No.: PCT/US2014/042947
§ 371 (c)(1),
(2) Date: Dec. 16, 2016

(87) PCT Pub. No.: WO2015/195117
PCT Pub. Date: Dec. 23, 2015

(65) Prior Publication Data
US 2017/0152272 A1    Jun. 1, 2017

(51) Int. Cl.
*C07F 3/06*    (2006.01)
(52) U.S. Cl.
CPC ............ *C07F 3/06* (2013.01); *C07B 2200/13* (2013.01)
(58) Field of Classification Search
CPC ........................................................ C07F 3/06
USPC ........................................................ 556/134
See application file for complete search history.

(56) References Cited

U.S. PATENT DOCUMENTS

| | | | |
|---|---|---|---|
| 9,498,421 | B2 | 11/2016 | Touhey et al. |
| 9,504,858 | B2 | 11/2016 | Yuan et al. |
| 2014/0170086 | A1 | 6/2014 | Pan et al. |
| 2015/0313821 | A1 | 11/2015 | Yuan et al. |
| 2015/0313822 | A1 | 11/2015 | Pan et al. |
| 2015/0313827 | A1 | 11/2015 | Hardy et al. |
| 2015/0328095 | A1 | 11/2015 | Pan et al. |
| 2015/0328110 | A1 | 11/2015 | Pan et al. |
| 2015/0328111 | A1 | 11/2015 | Liu et al. |
| 2015/0328112 | A1 | 11/2015 | Xu et al. |
| 2015/0328117 | A1 | 11/2015 | Pan et al. |
| 2015/0328118 | A1 | 11/2015 | Pan et al. |
| 2015/0335552 | A1 | 11/2015 | Liu et al. |
| 2015/0335553 | A1 | 11/2015 | Pan et al. |
| 2015/0335554 | A1 | 11/2015 | Pan et al. |
| 2015/0342851 | A1 | 12/2015 | Liu et al. |

FOREIGN PATENT DOCUMENTS

| | | |
|---|---|---|
| WO | WO 2015/195118 | 12/2015 |
| WO | WO 2015/195124 | 12/2015 |

OTHER PUBLICATIONS

Hartwell et al., 1970, "Preparation and Characterization of Tyrosine and Lysine Metal Chelate Polyesters and Polyamides," J. of the American Chemical Society 92(5):1284-1289.
International Search Report and Written Opinion of the International Searching Authority in PCT/US2014/042947, mailed Aug. 22, 2014.

*Primary Examiner* — Porfirio Nazario Gonzalez

(57) ABSTRACT

The disclosure provides an improved synthesis for a zinc-lysine complex having the formula $[Zn(C_6H_{14}N_2O_2)_2Cl]^+$ $Cl^-$, in which a zinc compound selected from ZnO and $ZnCl_2$, is reacted with a lysine compound selected from lysine and lysine.HCl, in aqueous acid. The disclosure also provides oral care and personal care compositions comprising the complex prepared by the synthesis, and methods of using these complexes and compositions.

20 Claims, No Drawings

LOW PH SYSNTHESIS OF ZINC-LYSINE COMPLEX

BACKGROUND

A zinc-lysine complex ("ZLC") having the chemical structure $[Zn(C_6H_{14}N_2O_2)_2Cl]^+Cl^-$, has recently been described. See, e.g. International Patent Application Nos. PCT/US2012/70489 and PCT/US2012/70498, filed on 19 Dec. 2012, incorporated by reference in its entirety. ZLC has the unusual property that under conditions of increasing dilution rather than going into or remaining in solution as the solution becomes more dilute, as would typically be the case for an ionic complex, the ZLC hydrolyzes, to provide a relatively insoluble zinc oxide precipitate. The ZLC is useful in antiperspirant products, as it precipitates under sweat conditions that can plug the pores and block sweat release. In the presence of protein, the ZLC will flocculate and plug the sweat glands. The zinc oxide precipitate can also inhibit odor-causing bacteria, making ZLC useful as a deodorant. ZLC is also useful in skin care products, for example liquid hand soap or body wash, providing controlled deposition of zinc oxide on the skin upon dilution and use, which has an antibacterial effect, and also may help protect against sun damage. Finally ZLC can be incorporated in oral care formulations, which upon use and dilution, provide a zinc oxide precipitate that is effective for inhibiting and treating dentinal hypersensitivity, dental caries, and enamel erosion and demineralization.

Prior syntheses of ZLC involved adding solid ZnO to a solution of lysine.HCl in water under near-neutral conditions; stirring for 12 hours; centrifugation to remove unreacted solids, and precipitation of ZLC by pouring the solution into ethanol. This procedure possess several disadvantages, including long reaction time, and extra steps for removal of the unreacted insoluble reagents, which results in excess amino acid in the final reaction mixture hindering product purity, in turn requiring further isolation with ethyl alcohol, and thus limiting feasibility on a large manufacturing scale. Thus, it can be seen that there is a need for improved methods for producing ZLC.

BRIEF SUMMARY

The disclosure provides synthetic methods for the production of ZLC. In some embodiments, the disclosure provides a synthetic method comprising the step of combining a zinc compound selected from ZnO and ZnCl$_2$, with a lysine compound selected from lysine and lysine.HCl, in aqueous acid, preferably wherein the pH of the reaction mixture is 6.3 or less, more preferably 6 or less; and preferably wherein the molar ratio of the zinc compound to the lysine compound is 3:1 to 1:3, e.g., 1:1 to 1:3, e.g., approximately 1:2. While a molar ratio in the range of 1:2 zinc compound to lysine compound is preferred for formation of material which is pure or near pure ZLC, in some embodiments, it may be desirable to have an excess of zinc, so that the final product is a mixture of ZLC and other zinc species. Thus in some embodiments, the molar ratio of the zinc compound to the lysine compound is 2:1 to 1:2.

The formation of the ZLC complex in aqueous acid is faster, more efficient and results in a more pure product than prior synthetic procedures.

DETAILED DESCRIPTION

The following description of the preferred embodiment(s) is merely exemplary in nature and is in no way intended to limit the disclosure, its application, or uses.

The disclosure therefore provides, in a first embodiment, a synthetic method (Method 1) which comprises the step of combining a zinc compound selected from ZnO and ZnCl$_2$, with a lysine compound selected from lysine and lysine.HCl, in aqueous acid, e.g., 1.1. Method 1, wherein the aqueous acid has a pH of 6.3 or less, for example 6 or less.

1.2. Any of the foregoing methods, wherein the aqueous acid comprises aqueous hydrochloric acid in a molar equivalent of 0.4 or greater, for example 0.4-1; for example 0.5.

1.3. Any of the foregoing methods, wherein the molar ratio of the zinc compound to the lysine compound is 3:1 to 1:3, e.g., 1:1 to 1:3, e.g., approximately 1:2.

1.4. Any of the foregoing methods wherein the molar ratio of the zinc compound to the lysine compound is 2:1 to 1:2.

1.5. Any of the foregoing methods, wherein combining the zinc compound with the lysine compound is performed by the steps of a) preparing an aqueous solution comprising the lysine compound and the hydrochloric acid; and b) adding the zinc compound to the solution; to form an initial reaction mixture.

1.6. Any of the foregoing methods, further comprising waiting a period of time sufficient to allow a zinc-lysine complex of formula $[Zn(C_6H_{14}N_2O_2)_2Cl]^+Cl^-$ to form; thereby forming a final reaction mixture.

1.7. Any of the foregoing methods, wherein the pH of the initial reaction mixture is 6.3 or less; for example 6 or less.

1.8. Any of the foregoing methods, wherein the pH of the initial reaction mixture is 5 to 6.

1.9. Any of the foregoing methods, wherein the pH of the final reaction mixture is 6 or less.

1.10. Any of the foregoing methods, wherein the molar ratios of the zinc compound:lysine compound:HCl are 1:(1-3):(0.4-1); for example 1:2:0.5.

1.11. Any of the foregoing methods, wherein the % solids in the initial reaction mixture is from 10%-60%.

1.12. Any of the foregoing methods, wherein the reaction is performed at ambient temperature.

1.13. Any of the foregoing methods, further comprising the step of isolating a zinc-lysine complex of formula $[Zn(C_6H_{14}N_2O_2)_2Cl]^+Cl^-$ from the final reaction mixture.

1.14. Method 1.9, where the isolation comprises crystallization from aqueous ethanol.

1.15. Method 1.9, where the isolation comprises spray drying the final reaction mixture.

1.16. Method 1.9, where the isolation comprises adjusting the pH of the final reaction mixture to near neutral; and forming crystals by evaporation of the mixture.

1.17. Any of the foregoing methods, wherein the zinc compound is ZnCl$_2$, and the lysine compound is lysine.

1.18. Any of the foregoing methods, wherein the zinc compound is ZnCl$_2$, and the lysine compound is lysine.HCl.

1.19. Any of the foregoing methods, wherein the zinc compound is ZnO, and the lysine compound is lysine.HCl.

1.20. Any of the foregoing methods, wherein the zinc compound is ZnO, and the lysine compound is lysine.

In a further embodiment, the disclosure provides a zinc-lysine complex (Complex 2) formed by any of the methods 1-1.18. For example, the disclosure provides:

2.1. Complex 2, in crystalline form.
2.2. Complex 2, in the form of a hydrate.
2.3. Complex 2, in the form of a hydrate having the formula [Zn(Lysine)$_2$Cl]Cl.H$_2$O.
2.4. Complex 2, having a structure wherein the Zn cation is coordinated by two lysine ligands with two nitrogen atoms from alpha NH$_2$ groups of the two lysine ligands and two oxygen atoms from carboxylic groups of the two lysine ligands in an equatorial plane, having a distorted square-pyramidal geometry with the apical position occupied by a chlorine atom, to form a positive cation moiety, with which a chloride anion is combined to form an ionic salt.

The disclosure further provides a personal care composition (Composition 1) for application to the skin, comprising any of Complexes 2-2.6, in combination with a cosmetically acceptable carrier. For example, the disclosure provides an antiperspirant or deodorant product comprising any of Complexes 2-2.6, in combination with a cosmetically acceptable carrier, or a liquid soap, for example a hand soap or body wash, comprising any of Complexes 2-2.6, in combination with a cosmetically acceptable carrier.

The disclosure further provides methods of reducing perspiration comprising applying an antiperspirant effective amount of any of Complexes 2-2.6 to the skin, methods of reducing body odor comprising applying a deodorant-effective amount of any of Complexes 2-2.6 to the skin, and methods of killing bacteria comprising contacting the bacteria with an antibacterially effective amount of any of Complexes 2-2.6.

The disclosure further provides (i) the use of any of Complexes 2-2.6, to kill bacteria, reduce perspiration, and/or reduce body odor; (ii) the use of any of Complexes 2-2.6, in the manufacture of a composition to kill bacteria, reduce perspiration, and/or reduce body odor; and (iii) any of Complexes 2-2.6, for use in killing bacteria, reducing perspiration, and/or reducing body odor.

The disclosure further provides an oral care composition (Composition 2), e.g., a toothpaste or a mouth rinse, which comprises any of Complexes 2-2.6, e.g., which upon use and dilution, provides a zinc oxide precipitate that is effective for inhibiting and/or treating an indication selected from dentinal hypersensitivity, dental caries, and enamel erosion and demineralization.

In another embodiment, the disclosure provides methods of inhibiting and/or treating an indication selected from dentinal hypersensitivity, dental caries, and enamel erosion and demineralization, comprising applying Composition 2 or an effective amount of any of Complexes 2-2.6 to the teeth. The disclosure further provides (i) the use of any of Complexes 2-2.6, for inhibiting and/or treating an indication selected from dentinal hypersensitivity, dental caries, and enamel erosion and demineralization; (ii) the use of any of Complexes 2-2.6, in the manufacture of a composition for inhibiting and/or treating an indication selected from dentinal hypersensitivity, dental caries, and enamel erosion and demineralization.

It has been discovered in accordance with the present disclosure that ZLC can be prepared by reacting a zinc compound selected from ZnO and ZnCl$_2$, with a lysine compound selected from lysine and lysine.HCl, in aqueous acid, for example aqueous HCl, preferably wherein the pH of the reaction mixture is 6.3 or less, more preferably 6 or less.

The methods of the disclosure provide ZLC having improved purity, yield and scalability as compared to prior synthetic procedures wherein the reaction is performed at near-neutral (i.e., above approximately pH 6.3 to about pH 7.4).

The methods of the disclosure are broadly applicable to preparation of ZLC from several zinc-containing and lysine-containing precursors. Preferably, the zinc-containing compound is ZnO or ZnCl$_2$, and the lysine-containing compound is lysine or lysine.HCl. Thus, in some embodiments the reagents are ZnCl$_2$ and lysine; or ZnCl$_2$ and lysine.HCl; or ZnO and lysine; or ZnO and lysine.HCl.

Generally, the molar ratio of the zinc-containing compound to the lysine-containing compound is from 1:1 to 1:3; preferably approximately 1:2.

Typically, an aqueous solution of the lysine-containing compound, for example lysine.HCl, is prepared and approximately 0.4-1 molar equivalent of acid, preferably about 0.5 molar equivalent, is added. The acid can be provided by, for example, addition of concentrated HCl to the solution of the lysine-containing compound. The zinc-containing compound, ZnO or ZnCl$_2$, is then added to the solution. Preferably, the amount of acid added will be sufficient to ensure that the pH of the reaction mixture is 6.3 or less, preferably 6 or less. While not wishing to be bound by any particular theory, it is believed that performing the reaction under mildly acidic conditions will rapidly solubilize the zinc containing compound, for example ZnO, thus allowing the reaction to proceed at a much faster rate, and with higher yield, than previous syntheses, which did not employ the acidic conditions of the present methods.

The reaction can be performed at a variety of temperature conditions. Typically, it is most convenient to perform the reaction at ambient temperature, i.e., approximately 25° C. The reaction is allowed to proceed until complete dissolution of the reactants—i.e. until the solution is completely clear. This typically takes from a few minutes to several hours, depending upon the specific reaction conditions such as temperature and scale.

Isolation of the ZLC complex can be accomplished by multiple routes depending upon the desired application. Significantly, no filtering or centrifugation steps are required prior to isolation of the final complex. For example, the reaction mixture, which is clear, can be stored for more than 3 months at slightly acidic pH (i.e., <pH 7) without precipitation of ZnO. Alternatively, the reaction mixture can be spray dried to a powder for a near 100% yield of all reaction components and easy measurement into a formulation. A crystalline salt of ZLC can be isolated upon adjustment of the pH of a concentrated reaction mixture with NaOH to near neutral (pH 6.8), and slow evaporation of the reaction mixture.

It will be understood that, although the ZLC may be primarily in the form of a complex, there may be some degree of equilibrium with the zinc compound (zinc oxide or zinc chloride) and the lysine compound (lysine or lysine hydrochloride) precursor materials, so that the proportion of material which is actually in complex compared to the proportion in precursor form may vary depending on the precise conditions of formulation, concentration of materials, pH, presence or absence of water, presence or absence of other charged molecules, and so forth.

ZLC, e.g., any of Complex 2, et seq., can be incorporated into a suitable base, for example a stick, roll-on, spray or aerosol for application to the underarm. Following application, the ZLC in the presence of charged molecules such as proteins found on the skin, the ZLC has a low zeta potential, and will flocculate, forming plugs which block sweat release. Additional water from sweat can moreover dilute the formulation, causing the complex to decompose, resulting in precipitation of zinc oxide, which can reduce sweat and odor as described above. Similarly, if the ZLC is provided in a hand soap or body wash base, the dilution of the ZLC upon washing results in a thin deposition of zinc oxide on the skin, providing an antibacterial effect.

As used herein, the term antiperspirant can refer to any material that can form a plug in a pore to reduce sweating, or antiperspirant refers to those materials classified as antiperspirants by the Food and Drug Administration under 21 CFR part 350. Antiperspirants may also be deodorants, particularly in the case of this disclosure, as zinc has antibacterial properties and can reduce odor-causing bacteria on the skin.

The composition can include the ZLC, e.g., any of Complex 2, et seq. and/or precursors thereof, for example zinc oxide, zinc chloride, lysine and lysine hydrochloride. In one embodiment, the ZLC is prepared at room temperature by mixing the precursors in an aqueous acidic solution. The in situ formation provides ease of formulation. The precursors can be used instead of first having to form the ZLC. In another embodiment, the water permitting formation of the ZLC, e.g., any of Complex 2, et seq. from the precursor comes from sweat that comes into contact with the composition after application.

In certain embodiments, the amount of ZLC, e.g., any of Complex 2, et seq. in the composition of the disclosure, e.g., Compositions 1, is 0.05 to 10% by weight of the composition. In certain embodiments, precursors, e.g., zinc oxide and lysine hydrochloride, are present in amounts such that when combined into the ZLC, e.g., any of Complex 2, et seq., the ZLC, e.g., any of Complex 2, et seq. would be present in an amount of 0.05 to 10% by weight of the composition. In either of these embodiments, the amount of the ZLC, e.g., any of Complex 2, et seq. can be varied for the desired purpose, such as an antibacterial agent or as an antiperspirant. In other embodiments, the amount of the ZLC, e.g., any of Complex 2, et seq. is at least 0.1, at least 0.2, at least 0.3, at least 0.4, at least 0.5, at least 1, at least 2, at least 3, or at least 4 up to 10% by weight of the composition. In other embodiments, the amount of the ZLC, e.g., any of Complex 2, et seq. is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In some embodiments, the total amount of zinc in the composition is 0.05 to 8% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition.

In certain embodiments, the composition is anhydrous. By anhydrous, there is less than 5% by weight water, optionally less than 4, less than 3, less than 2, less than 1, less than 0.5, less than 0.1 down to 0% by weight water.

When provided in an anhydrous composition, precursors, e.g., zinc oxide and lysine hydrochloride, will not significantly react to form the ZLC, e.g., any of Complex 2, et seq. When contacted with a sufficient amount of water, which can be in the form of sweat, the precursors will then react to form the ZLC, e.g., any of Complex 2, et seq. The ZLC, e.g., any of Complex 2, et seq. when introduced into a sweat duct will flocculate with protein and/or hydrolyze with water and/or sweat to form a precipitate to block the sweat duct.

In certain embodiments, the ZLC, e.g., any of Complex 2, et seq. can have a zeta potential on the order of +10 to +60, e.g., between +20 and +50. Zeta potential is measured as described below. The zeta potential indicates the degree of repulsion between adjacent, similarly charged particles in a dispersion. For molecules and particles that are small enough to be influenced by van der Waals forces, a high zeta potential will tend to confer stability, i.e., the particles will tend to repel one another, and the solution or dispersion will resist aggregation. When the zeta potential is low, attraction exceeds repulsion and the dispersion will break and flocculate. Here, it is desirable to have a zeta potential that is high enough in formulation to deter aggregation, but low enough to allow flocculation and blockage of the pores. As shown in the examples below, the ZLC, e.g., any of Complex 2, et seq. has a zeta potential similar to aluminum chlorohydrate antiperspirants. Having a similar zeta potential, the ZLC, e.g., any of Complex 2, et seq. will behave similarly and flocculate when introduced into a pore and becomes hydrated. In contrast, zinc chloride has a zeta potential of about 0, which is much lower than current antiperspirant salts and the current disclosure.

In certain embodiments, the ZLC, e.g., any of Complex 2, et seq. can have a conductivity of greater than 8000, optionally greater than 9000, greater than 10,000, or greater than 12,000 μS/cm.

The personal care composition can be any type of composition. In certain embodiments, the composition is any composition in which it is desired to include an antibacterial agent for application to the skin. Examples of such compositions include, but are not limited to, personal care compositions, antiperspirants, deodorants, body washes, shower gels, bar soaps, shampoo, hair conditioners, and cosmetics.

The carrier represents all other materials in the composition other than the ZLC, e.g., any of Complex 2, et seq. or the zinc oxide and amino acid hydrohalide. The amount of carrier is then the amount to reach 100% by adding to the weight of the ZLC, e.g., any of Complex 1, et seq. or the zinc oxide and amino acid hydrohalide.

For antiperspirant/deodorant compositions, the carrier can be any carrier that is used for antiperspirants/deodorants. The carrier can be in the form of a stick, a gel, a roll-on, or an aerosol. For stick formulations, the carrier may include oils and/or silicones and gelling agents. An example of a formulation can be found in US2011/0076309A1, incorporated by reference herein.

Optional ingredients that can be included in an antiperspirant and/or deodorant formulation of the compositions of the disclosure include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments. If desired, an antiperspirant and/or deodorant agent additional to the ZLC, e.g., any of Complex 2, et seq. can be included, for example an odor reducing agent such as a sulfur precipitating agent, e.g., copper gluconate, zinc gluconate, zinc citrate, etc.

The antiperspirant compositions can be formulated into topical antiperspirant and/or deodorant formulations suitable for application to skin, illustratively a stick, a gel, a cream, a roll-on, a soft solid, a powder, a liquid, an emulsion, a suspension, a dispersion or a spray. The composition can comprise a single phase or can be a multi-phase system, for example a system comprising a polar phase and an oil phase, optionally in the form of a stable emulsion. The composition can be liquid, semi-solid or solid. The antiperspirant and/or deodorant formulation can be provided in any suitable container such as an aerosol can, tube or container with a porous cap, roll-on container, bottle, container with an open end, etc.

The compositions can be used in a method to reduce sweating by applying the composition to skin. In certain embodiments, the application is to axilla. Also, the compositions can be used to kill bacteria by contacting bacteria with the composition. For example, in one embodiment, the combination of the amino acid or amino acid hydrohalide with the zinc oxide increases the availability of zinc ions, which can then kill bacteria and reduce sweat.

Thus the disclosure provides (i) a method for controlling perspiration comprising applying to skin an antiperspirant effective amount of a formulation of any embodiment embraced or specifically described herein, e.g., any of Compositions 1 et seq.; and (ii) a method for controlling odor from perspiration comprises applying to skin a deodorant effective amount of a formulation of any embodiment embraced or specifically described herein, e.g., any of Compositions 1 et seq.

In another embodiment, the disclosure provides oral care formulations, e.g., Composition 2, for example a toothpaste, gel, mouthwash, powder, cream, strip, or gum comprising an effective amount of the ZLC of the disclosure, e.g., any of Complex 2, et seq.

If the actives are delivered in the form of a mouthwash, a person desiring the benefits rinses with the stock solution and natural dilution of the stock solution by saliva will initiate the precipitation of the zinc. Alternatively, the person can mix the stock solution with appropriate amount of an aqueous diluent (such as approximately 1 part stock solution and 8 parts water for the zinc-lysine samples), and rinse with the mixture.

In another embodiment, the mixture is prepared and immediately transferred into a retaining tray, such as those used in holding whitening gels, and the person can wear the tray for the effective period of time. The teeth that are in contact with the mixture will be treated. For use with retaining tray, the mixture can be in the form of a low-viscosity liquid or a gel.

In another embodiment, the stock solution, or a mixture of stock solution with water, is applied to the teeth in a gel formulation, e.g., wherein the gel can stay on the tooth for an extended period of time for effective treatment.

In another embodiment, the ZLC active is provided in a toothpaste. Upon brushing, the active is diluted by saliva and water, leading to precipitation and the formation of deposits and occluding particles.

The rate of precipitation from the formulation can be modulated by adjusting concentration of the complex in the stock solution, and changing the ratio of the stock to water. A more diluted formula leads to faster precipitation and is thus preferred when a fast treatment is desired.

The benefits of the oral care compositions of the disclosure are numerous. By providing zinc ions and zinc containing compounds that can release zinc ions in oral cavities, the oral care compositions of the disclosure provide antimicrobial, antiplaque, antigingivitis, anti-malodor, anticaries, and anticalculus benefits. The occluding particles and the surface deposits are compounds containing zinc (particularly ZnO), as well as other zinc derivatives which can release zinc ions into oral cavities and provide the various benefits as recognized above. Additional benefits include but are not limited to anti-attachment, anti-periodontitis and anti-bone loss, as well as promotion of wound healing.

A second benefit is the antierosive properties of zinc ions, which form antierosive deposits on tooth surfaces through oxidation and hydrolysis. The surface deposits, as well as the occluding particles, can react with and neutralize acids, thus protecting the dental surface from the erosive effects of the acids. In this regard, the more surface depositions/occlusion the treatments lead to, the more efficacious the treatments are, and therefore zinc-arginine and zinc-lysine are preferred. It is also noted that when the surface deposits and occluding particles neutralize acids, beneficial zinc ions and the basic amino acid, lysine, are released, providing oral care benefits other than anti-erosion.

A third benefit is anti-sensitivity benefit as a result of the occlusion. Occlusion of dentin tubules leads to sensitivity relief.

A fourth benefit is the benefit associated with the lysine. The occluding particles and surface deposits contain not only zinc, but also lysine, which provides multiple benefits. For example, the basic amino acid leads to higher pH of the plaque and can provide anticaries benefits.

Unless stated otherwise, all percentages of composition components given in this specification are by weight based on a total composition or formulation weight of 100%.

Unless otherwise specifically identified, the ingredients for use in the compositions and formulations of the present disclosure are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this disclosure, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the disclosure extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Example 1—Synthesis and Characterization of Zinc-Lysine Complex ZLC

In accordance with the methods of the disclosure, a zinc compound selected from zinc oxide (ZnO) and zinc chloride ($ZnCl_2$) is reacted with a lysine compound selected from lysine and lysine hydrochloride (lysine.HCl) in acidic aqueous solution.

The general reaction for formation of ZLC in accordance with the present disclosure, as exemplified by the reaction of ZnO and lysine.HCl, is as follows:

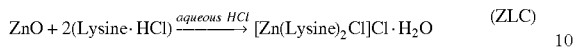

(ZLC)

Lysine.HCl (2 molar equivalents) was dissolved in deionized water with stirring at room temperature. Concentrated hydrochloric acid (HCl, 34-37%) equal to approximately 0.5 molar equivalent was added to the reaction mixture. ZnO (1 molar equivalent) was added to the vessel, and the resultant mixture was stirred until complete dissolution, typically minutes to a few hours. The pH of the reaction is kept at 6 or below.

The ZLC complex can be kept in solution in the final reaction mixture, which is clear, for more than 3 months at slightly acidic pH (i.e., <pH 7) without precipitation of ZnO. Alternatively, the reaction mixture can be spray dried to a powder, resulting in a near 100% yield of all reaction components; or the reaction mixture can be adjusted to a near-neutral pH (e.g., 6.8), and the crystalline salt of ZLC can be isolated upon slow evaporation of the concentrated ZLC reaction mixture.

ZLC complex prepared by reaction of lysine.HCl and ZnO in aqueous acid as described above was compared to ZLC prepared by a previous technique employing near-neutral conditions. The two samples are isolated by spray drying and analyzed by nuclear magnetic resonance (NMR) and infrared (IR) spectroscopy. NMR spectra of the spray product samples from the present and previous syntheses show identical proton environments under similar pH $D_2O$ solutions, confirming formation of the same ZLC complex. Comparative IR spectra of the two samples also show similar product formation.

The long-term stabilities of the final reaction mixtures were also compared. The presence of acid in the reaction mixture in accordance with the present method (HCl; with the pH of the reaction adjusted to below 6) showed a sustained clarity of the final reaction mixture after five months at ambient conditions, whereas the sample prepared under near-neutral conditions was nearly opaque due to precipitated solids.

Laboratory Scale-Up:

The reaction as described above can be performed with from 10%-60% (w/w) solids, with reaction time directly proportional to scale. For example, a 50% (w/w) reaction to synthesize ZLC (approximately 1.8 Kg theoretical yield) will take only minutes to hours to achieve clarity. The final zinc level is approximately 4.5%, which is higher than was obtained with the prior synthesis at near-neutral conditions (2.39%).

Example 2: Other Reagents

A series of reactions to generate ZLC is performed using different reagents. The results are shown in Table 1 below:

| Reaction | 1 | 2 | 3 | 5 | 7 | 8 | 9 | 10 |
|---|---|---|---|---|---|---|---|---|
| $ZnCl_2$(g) | 13.63 | 6.82 | 6.82 | 0 | 13.63 | 0 | 0 | 0 |
| ZnO (g) | 0 | 0 | 0 | 4.07 | 0 | 8.14 | 8.14 | 8.14 |
| Lysine(g) | 29.24 | 14.62 | 14.62 | 14.62 | 0 | 0 | 0 | 0 |
| Lysine·HCl | 0 | 0 | 0 | 0 | 36.53 | 36.53 | 36.53 | 36.53 |
| HCl (37%, g) | 0 | 2.9 | 0 | 11.05 | 0 | 0 | 0 | 5.8 |
| NaOH (g) | 0 | 0 | 0 | 0 | 6.6 | 6.6 | 0 | 0 |
| DI water | 200 | 100 | 100 | 100 | 200 | 200 | 200 | 200 |
| Temp. (° C.) | 25 | 25 | 50 | 25 | 25 | 50 | 25 | 25 |
| pH | 6.85 | 5.55 | 6.70 | 6.50 | 5.98 | 6.84 | 6.77 | 5.87 |
| Unreacted solid | Yes | No | Yes | Yes | No | Yes | Yes | No |

As these results show, in the reactions carried out below pH 6 there is no remaining unreacted solid, and these results appear independently of the reaction temperature or whether the zinc is zinc chloride or zinc oxide or whether the lysine is lysine free base or lysine hydrochloride.

We claim:

1. A synthetic method comprising the step of combining a zinc compound selected from ZnO and $ZnCl_2$, with a lysine compound selected from lysine and lysine.HCl, in aqueous acid.

2. The method of claim 1, wherein the aqueous acid has a pH of 6 or less.

3. The method of claim 1, wherein the aqueous acid comprises aqueous hydrochloric acid in a molar equivalent of 0.4 or greater.

4. The method of claim 1, wherein the molar ratio of the zinc compound to the Lysine compound is 1:1 to 1:3.

5. The method of claim 1, wherein the combining is performed by the steps of:
   a) preparing an aqueous solution comprising the lysine compound and the hydrochloric acid; and
   b) adding the zinc compound to the solution; to form an initial reaction mixture.

6. The method of claim 1, further comprising waiting a period of time sufficient to allow a zinc-lysine complex of formula $[Zn(C_6H_{14}N_2O_2)_2Cl]^+Cl^-$ to form; thereby forming a final reaction mixture.

7. The method of claim 1, wherein the pH of the initial reaction mixture is 6.3 or less.

8. The method of claim 1, wherein the pH of the initial reaction mixture is 5 to 6.

9. The method of claim 1, wherein the pH of the final reaction mixture is 6 or less.

10. The method of claim 1, wherein the molar ratios of the zinc compound:lysine compound:HCl are 1:(1-3):(0.4-1).

11. The method of claim 1, wherein the molar ratios of zinc compound:lysine compound:HCl are 1:2:0.5.

12. The method of claim 1, wherein the % solids in the initial reaction mixture is from 10%-60%.

13. The method of claim 1, wherein the reaction is performed at ambient temperature.

14. The method of claim 1, further comprising the step of isolating a zinc-lysine complex of formula [Zn$(C_6H_{14}N_2O_2)_2$ Cl]$^+$Cl$^-$ from the final reaction mixture.

15. The method of claim 1, where the isolation comprises crystallization from aqueous ethanol.

16. The method of claim 1, where the isolation comprises spray drying the final reaction mixture.

17. The method of claim 1, where the isolation comprises adjusting the pH of the final reaction mixture to near neutral, and forming crystals by evaporation of the mixture.

18. The method of claim 1, wherein the zinc compound is $ZnCl_2$, and the lysine compound is lysine.

19. The method of claim 1, wherein the zinc compound is ZnO, and the lysine compound is lysine.HCl.

20. The method of any of claim 1, wherein the zinc compound is ZnO, and the lysine compound is lysine.

* * * * *